US00PP15105P2

(12) United States Plant Patent
Allen et al.

(10) Patent No.: US PP15,105 P2
(45) Date of Patent: Aug. 24, 2004

(54) BETULA PLANT NAMED 'SUMMER CASCADE'

(50) Latin Name: *Betula*
Varietal Denomination: Summer Cascade

(75) Inventors: John D. Allen, Harmony, NC (US); Daniel A. Allen, Harmony, NC (US)

(73) Assignee: Shiloh Nursery, Harmony, NC (US)

( * ) Notice: Subject to any disclaimer, the term of this patent is extended or adjusted under 35 U.S.C. 154(b) by 0 days.

(21) Appl. No.: 10/191,662

(22) Filed: Jul. 8, 2002

(51) Int. Cl.[7] ..... A01H 5/00
(52) U.S. Cl. ..... Plt./216
(58) Field of Search ..... Plt./216

(56) References Cited

U.S. PATENT DOCUMENTS

| | | | | | |
|---|---|---|---|---|---|
| PP4,409 | P | * | 4/1979 | Cully | Plt./216 |
| PP6,192 | P | * | 5/1988 | SaBell | Plt./216 |
| PP10,963 | P | * | 6/1999 | Cheng et al. | Plt./216 |
| PP12,400 | P2 | * | 2/2002 | Pinney, Jr. | Plt./216 |
| PP12,749 | P2 | * | 7/2002 | Heims | Plt./216 |
| PP12,766 | P2 | * | 7/2002 | Pinney, Jr. | Plt./216 |
| PP12,767 | P2 | * | 7/2002 | Pinney, Jr. | Plt./216 |
| PP12,768 | P2 | * | 7/2002 | Pinney, Jr. | Plt./216 |

* cited by examiner

*Primary Examiner*—Bruce R. Campell
*Assistant Examiner*—W C Haas

(57) ABSTRACT

A new cultivar of Betula plant named 'Summer Cascade', that is characterized by flexible new shoot growth and pendulous branches. In combination these traits set 'Summer Cascade' apart from all other existing varieties of Betula known to the inventor.

4 Drawing Sheets

Botanical designation: The Latin name of this novel cultivar is *Betula nigra* L. with the cultivar name 'Summer Cascade'.

BACKGROUND OF THE INVENTION

The present invention relates to a new and distinct cultivar of Betula grown for use as a large shrub to medium sized tree.

'Summer Cascade' is a seedling of unknown parentage. The new cultivar was discovered by the inventor in a cultivated area of Harmony, N.C., in 1996 from a group of seedlings originally planted in 1992. 'Summer Cascade' is distinguished from all other Betula known to the inventor by its mounding habit and unique pendulous form and was selected by the inventor based on the seedlings unusual mounded habit with shoots from successive years forming arching layers of branches.

Dr. Thomas Ranney at North Carolina State University, Fletcher, N.C., USA first propagated 'Summer Cascade' by asexual grafting in February 2001. The characteristics of the new cultivar have been determined stable and are reproduced true to type in successive generations.

SUMMARY OF THE INVENTION

The following traits have been repeatedly observed and represent the characteristics of the new Betula cultivar 'Summer Cascade'. These traits in combination distinguish 'Summer Cascade' from all other commercial varieties known to the inventor. 'Summer Cascade' has not been tested under all possible conditions and phenotypic differences may be observed with variations in environmental, climatic and cultural conditions.

1. Betula 'Summer Cascade' exhibits a unique pendulous form.
2. Betula 'Summer Cascade' exhibits flexible new shoot growth.

3. Betula 'Summer Cascade' exhibits a mounded habit when grown free-form.
4. Betula 'Summer Cascade' exhibits arching layers of branches in successive years when grown free-form.
5. Betula 'Summer Cascade' may be staked or trained to different shapes including a straight or sinuous trunk with pendulous branches.
6. Betula 'Summer Cascade' is 1.8 meters tall and 3 meters wide at 10 years when grown free-form.
7. Betula 'Summer Cascade' is a large shrub to medium size tree suitable for landscape use.
8. Betula 'Summer Cascade' is strongly vigorous.
9. Betula 'Summer Cascade' is expected to be hardy in USDA Zones 4–9.

BRIEF DESCRIPTION OF THE DRAWINGS

The accompanying drawings illustrate the distinguishing traits of the new Betula cultivar 'Summer Cascade'.

The first drawing was made April 2002 and illustrates the entire plant grown from a 15 cm. tall rooted cutting that was trained to have a sinuous trunk and demonstrates initial branch angles, form of a young tree and young foliage following 3 months of growth in a greenhouse in a 19 liter container.

The second drawing was made September 2001 and is of a grafted tree, started as a 10 cm. long scion grafted on a 1 meter tall standard understock that was trained to a straight central trunk and demonstrates the foliage and pendulous habit of the lateral branches at the end of one growing season in a greenhouse in a 19 liter container which was grafted in February 2001.

The third drawing was made March 2002 prior to budbreak and depicts a dormant grafted tree, started as a 10 cm. long scion grafted on a 1 meter tall standard understock, that was trained to a straight central trunk and demonstrates the branch structure, angle of branch attachment, and pendulous habit of the lateral branches following one season of growth in a greenhouse in a 38 liter container which was grafted in February 2001.

The fourth drawing was made in April 2002 and illustrates the flexible new shoots. The drawings were made of plants grown in Fletcher, N.C. The drawings were made using conventional techniques and although colors may appear different from actual colors due to light reflectance they are as accurate as possible by conventional photography.

BOTANICAL DESCRIPTION OF THE PLANT

The following is a detailed description of 'Summer Cascade' after 10 years as grown in Harmony, N.C., USA. The color determinations are in accordance with The 2001 Edition of The R.H.S. Color Chart of The Royal Horticultural Society, London, England, except where general color terms of ordinary dictionary significance are used. Where dimensions, color and other characteristics are given, it is to be understood that such characteristics are approximations of averages and ranges as measured in Fletcher, N.C. and are as accurately reported as practicable. Where sizes are given, it is to be understood that such characteristics are approximations of averages and ranges as measured in Harmony, N.C. Growing conditions, diseases and pests are similar to that of other Betula. There are no growing problems known to the inventor. When left untrained, this cultivar becomes a large mounded shrub or small tree. The form of the original plant is a broad mound with multiple layers of arching branches. The flexible new shoots allow the tree to be trained to different shapes and forms including use in topiary. This tree can be grown with single or multiple trunks.

Botanical classification: *Betula nigra* 'Summer Cascade'.

Species: *nigra.*

Commercial classification: The new cultivar serves as a large shrub to medium sized tree.

Use: Landscape.

Cultural requirements: Plant in full sun or partial shade and is best adapted to moist fertile soil with acid level of 6.5 and below. The plant must be staked or trained to develop a tree form.

Parentage: *Betula nigra* 'Summer Cascade' is a seedling of unknown parentage.

Description:

*Classification.*—Tree.

*Type.*—Deciduous.

*Bloom period.*—To date no blooms have been observed.

*Vigor.*—Rapid growth. 2 to 3 meters per growing season if staked.

*Armature.*—None.

*Height.*—1.8 meters (potentially 23 meters at maturity).

*Width.*—3.0 meters.

*Hardiness.*—USDA Zones 4 to 9.

*Diseases and pests.*—None have been observed on plants growing in Fletcher, N.C.

*Propagation.*—Propagation is accomplished using stem cuttings, grafting or tissue culture.

*Trunk.*—Size (outside diameter): 5 cm. measured 30 cm. from the ground on a 2-year-old tree grown outdoors in Fletcher, N.C. from a 15 cm. tall rooted cutting.

*Bark.*—Color: Young branches: Including 165A and 165B. Larger branches and trunk: Outside: Varies from grayish white (including 155D, 156D and 156C) to gray orange (including 164C and 164D). Inside: Golden brown (including 165A and 165C). Exfoliation/Texture: Bark is smooth initially then becomes increasingly course with increasing trunk diameter. Bark begins to exfoliate on 1–1.5 cm. diameter branches with papery sheets on larger branches and stems.

*Shoots.*—Spacing: Irregular. Arrangement: Alternate. Color: Initially: 143C. Older shoots: 199B. Surface: Initially pubescent, then becoming glabrous. Size (outside diameter): Lateral shoots can attain a diameter of 1–2 cm. in diameter, in one growing season, where they attach to the trunk. Angle of Attachment: Initially: 35 to 45 degrees. Older shoots: 60 to 90 degrees. Lenticels: Number: Numerous (18–25 per sq. cm. on 0.5 cm. diameter shoots, 15–20 per sq. cm. on 2.0 cm. diameter shoots). Color: 164D. Size: Varied (0.5 to 2.0 mm in length).

*Foliage.*—Type: Simple. Size (varies in size depending on the environment and time of year): Length: 3 to 11 cm. Width: 1.5 to 9 cm. Arrangement: Alternate. Shape: Rhombic-ovate. Division: Simple. Apex: Acute. Base: Acute to truncate. Venation: Type: Pinnate. Number: 7 to 11 pairs. Color: Yellow green 144B (above) and 139C to N138 (below). Margins: Doubly serrate. Surface: Color: Young: Light green 143C (above) and 139C to N138C (below). Fully developed: Medium to dark green, 137C to 137A, (above) and 139C to N138C (below). Texture: Adaxial: glabrous. Abaxial: glaucous. Attachment: Petiolate. Petiole (slightly pubescent): Length: 0.5 to 1.5 cm. Diameter: 1–2 mm at base. Color: Greyed orange 166C–166A. Buds: Type: Imbricate. Length: 0.4 to 0.6 cm. Color: 165A.

Reproductive organs: No flowers have been observed on any of these plants at this time.

Seed production: No seeds have been observed on any of these plants at this time.

Comparison with other cultivars: *Betula nigra* 'Summer Cascade' differs from other known cultivars of *Betula nigra,* including 'BNMTF', 'Little King', 'Graceful Arms', 'Cully', U.S. Plant Pat. No. 4,409, and 'Suwanee', with its strongly pendulous branches and weeping form.

What is claimed is:

1. A new and distinct cultivar of Betula plant named 'Summer Cascade' as described and illustrated herein.

* * * * *

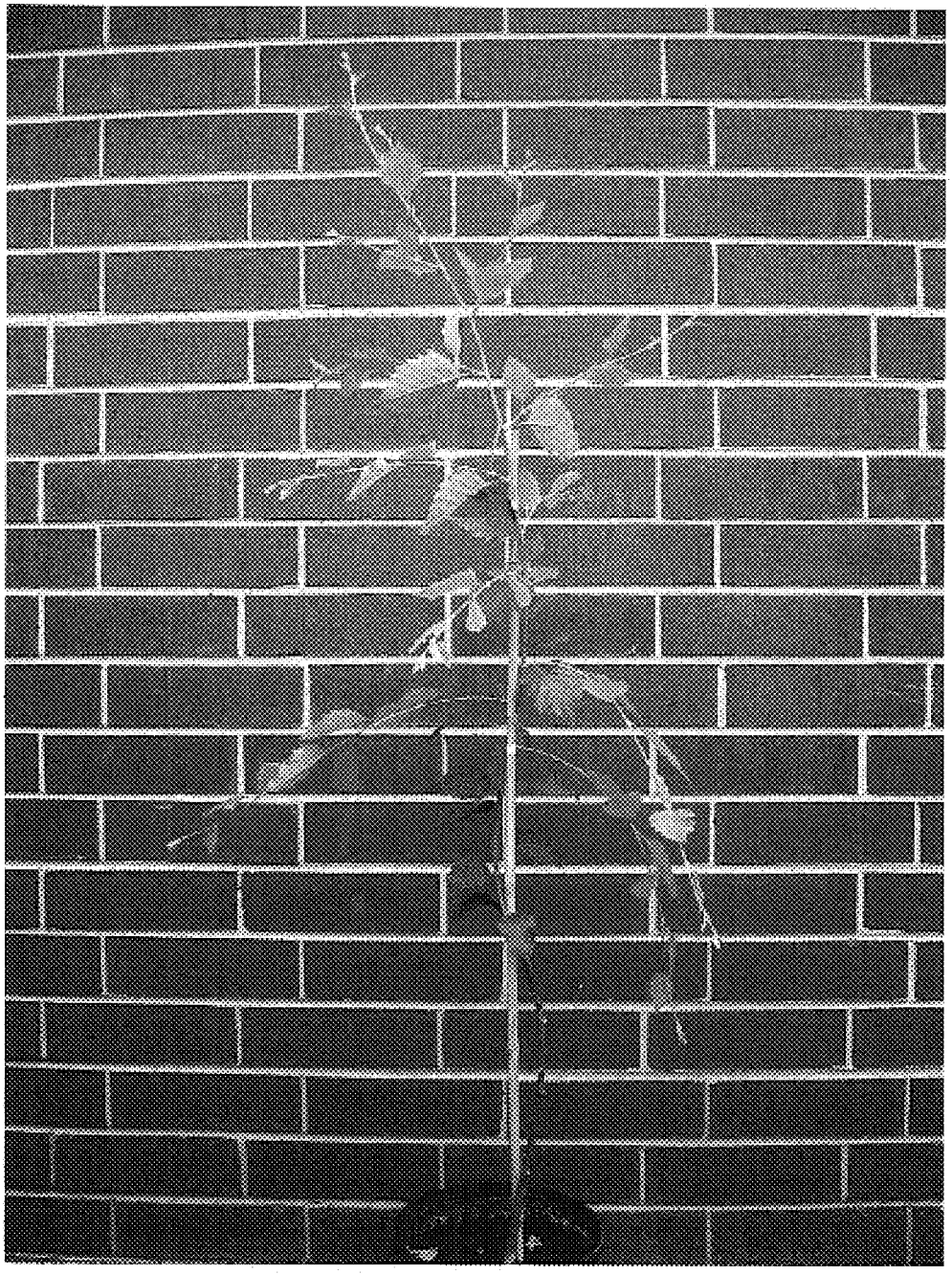

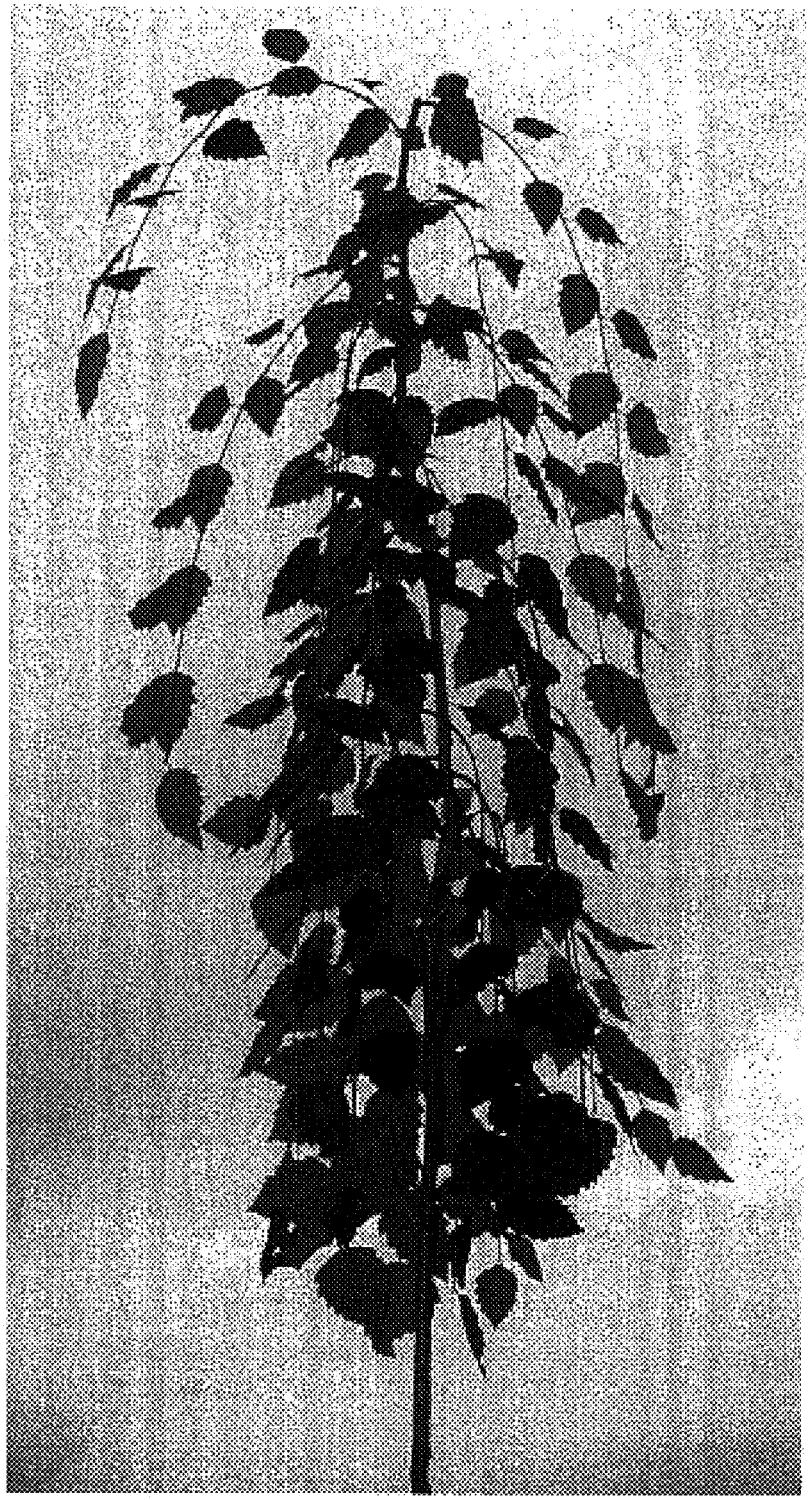

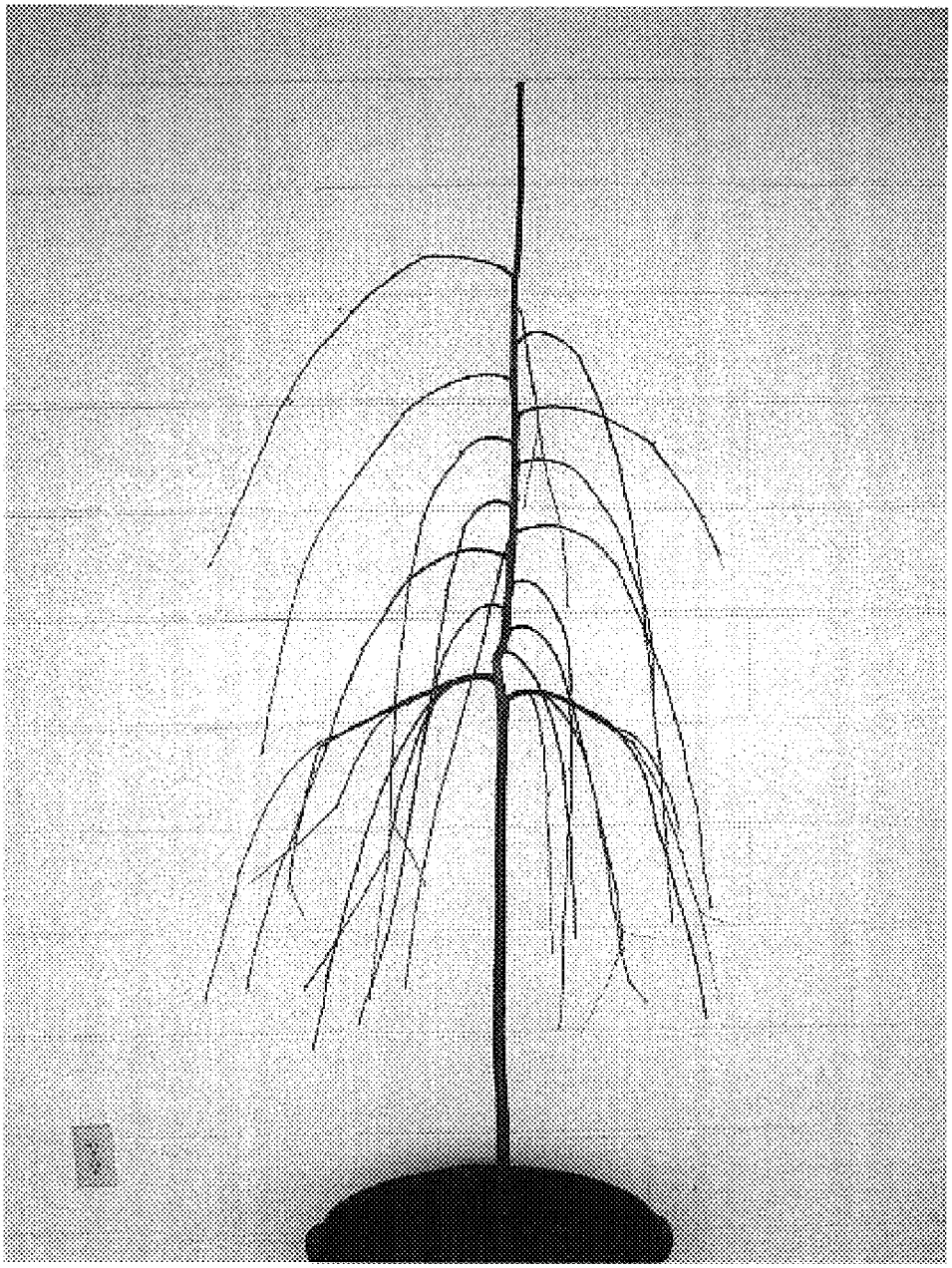

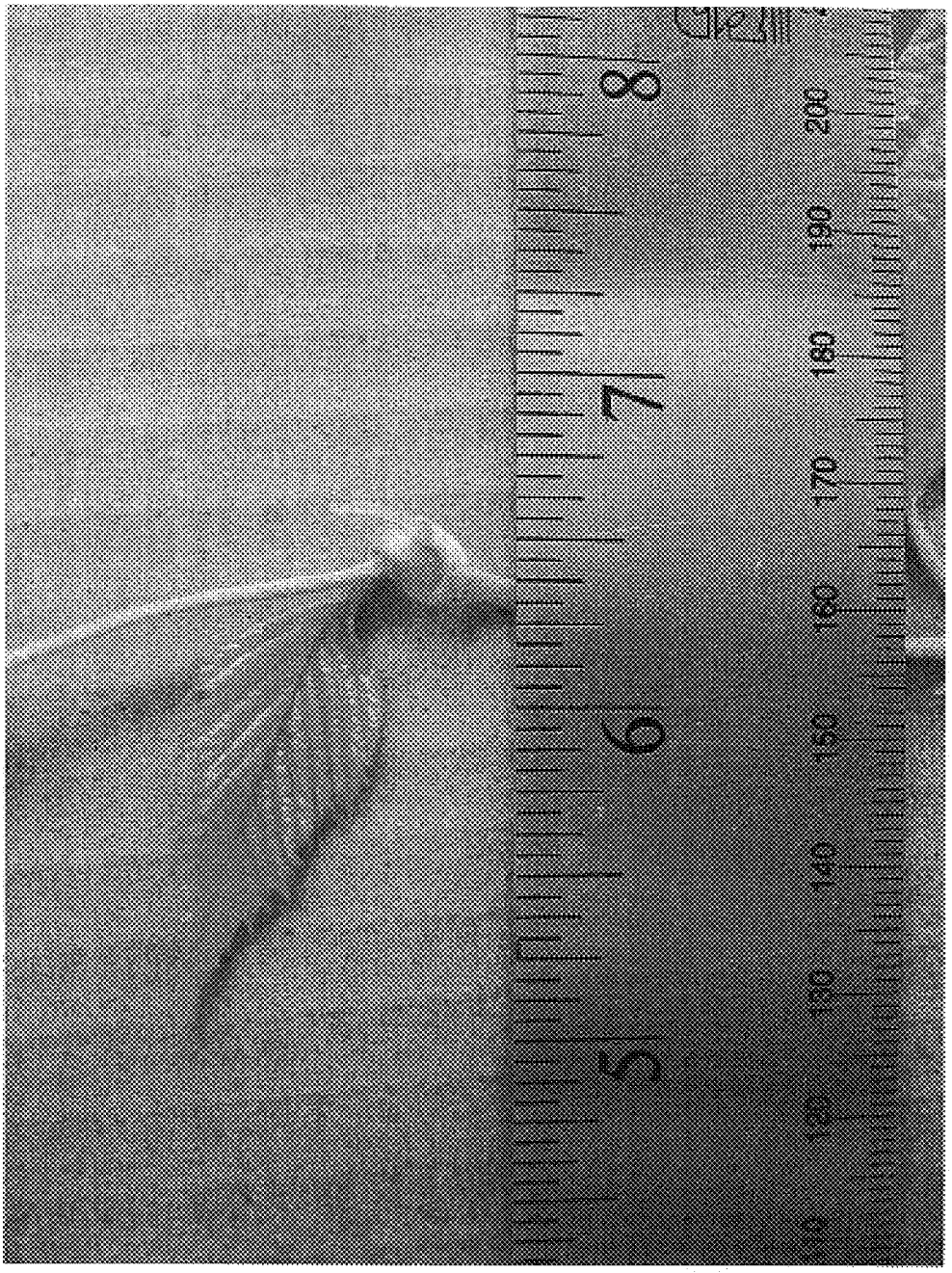
110
120
130
140
150
160
170
180
190
200
5
6
7
8